(12) United States Patent
Claflin et al.

(10) Patent No.: US 11,066,349 B2
(45) Date of Patent: Jul. 20, 2021

(54) METHOD FOR SEPARATING ESSENTIAL OILS FROM BIOMASS

(71) Applicant: Oli Extraction Company, Cumberland, RI (US)

(72) Inventors: Gregory Carl Claflin, Cumberland, RI (US); Jessica McGowan Claflin, Cumberland, RI (US); Katrina Melissa McGowan Claflin, Cumberland, RI (US)

(73) Assignee: Oil Extraction Company, Cumberland, RI (US)

( * ) Notice: Subject to any disclaimer, the term of this patent is extended or adjusted under 35 U.S.C. 154(b) by 0 days.

(21) Appl. No.: 16/873,897

(22) Filed: Aug. 6, 2020

(65) Prior Publication Data

US 2021/0053899 A1  Feb. 25, 2021

Related U.S. Application Data

(60) Provisional application No. 62/922,609, filed on Aug. 19, 2019.

(51) Int. Cl.
| | |
|---|---|
| *C07C 37/82* | (2006.01) |
| *C07C 37/74* | (2006.01) |
| *B01D 11/00* | (2006.01) |
| *B01D 11/02* | (2006.01) |
| *C07C 37/68* | (2006.01) |

(52) U.S. Cl.
CPC .......... *C07C 37/82* (2013.01); *B01D 11/0242* (2013.01); *B01D 11/0288* (2013.01); *B01D 11/0296* (2013.01); *C07C 37/685* (2013.01); *C07C 37/74* (2013.01)

(58) Field of Classification Search
CPC ....... C07C 37/82; C07C 37/74; C07C 37/685; B01D 11/00
See application file for complete search history.

(56) References Cited

U.S. PATENT DOCUMENTS

| | | | |
|---|---|---|---|
| 2016/0228787 A1* | 8/2016 | Payack | B01D 3/343 |
| 2020/0054962 A1* | 2/2020 | Vanaman | B01D 11/0288 |
| 2020/0063061 A1* | 2/2020 | Vanaman | C11B 1/106 |
| 2020/0188812 A1* | 6/2020 | Galyuk | C11B 9/025 |

OTHER PUBLICATIONS

Apeks Supercritical, "How to Extract CBD—The Extraction Process & HowCBD Oil is Made" downloaded Jul. 5, 2019.

* cited by examiner

*Primary Examiner* — Sikarl A Witherspoon
(74) *Attorney, Agent, or Firm* — Michael de Angeli

(57) ABSTRACT

Essential oils, such as CBD oil, are extracted from biomass, such as hemp, in a continuous process. The biomass is delivered to the upper end of a vertically oriented extraction chamber, while a solvent is injected at the lower end thereof. As the solvent flows upwardly, the oil is removed from the biomass. The resulting liquor is collected and purified.

11 Claims, 8 Drawing Sheets

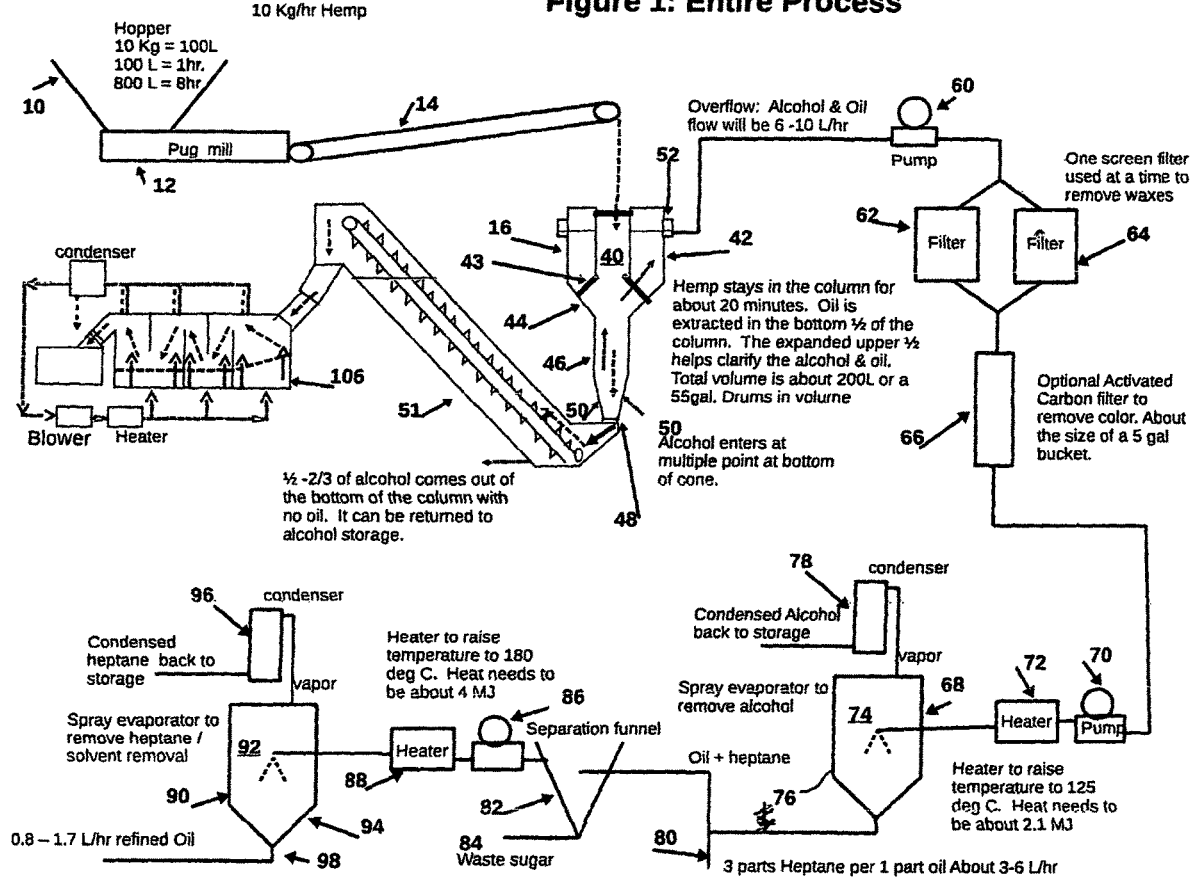
Figure 1: Entire Process

Figure 2: Milling
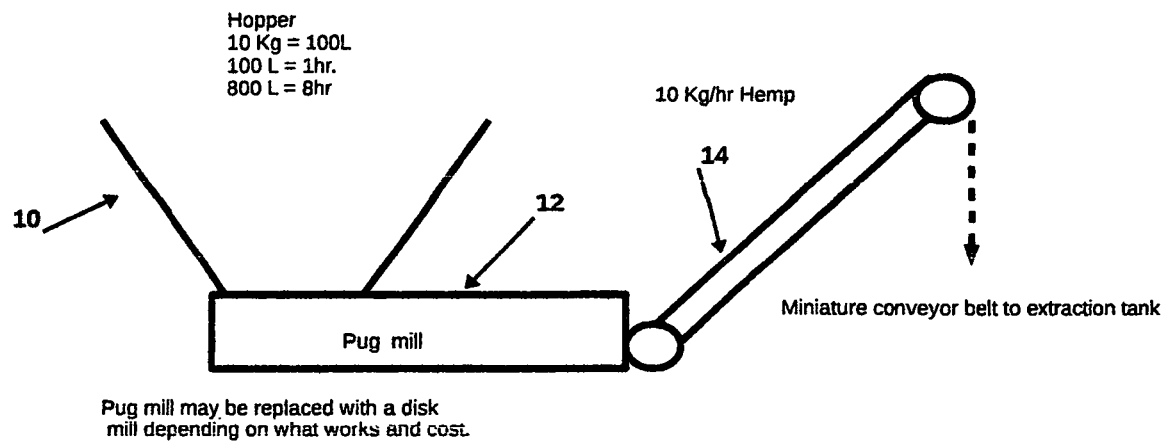

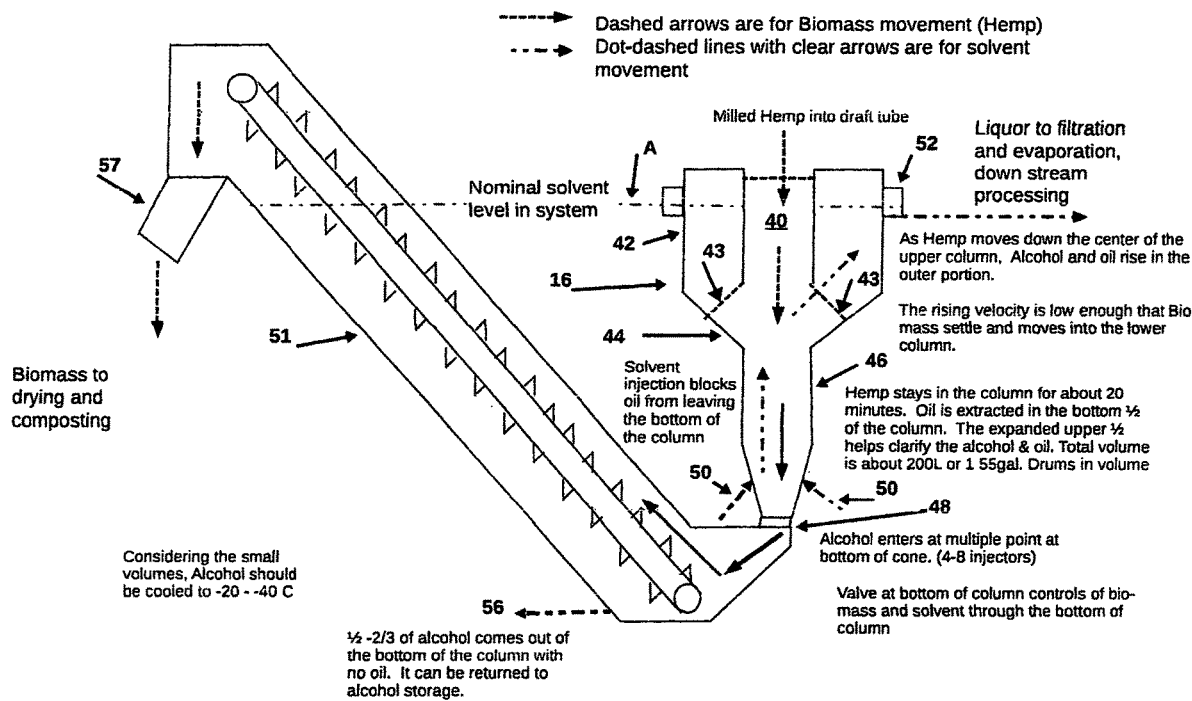
Figure 3: Oil Extraction

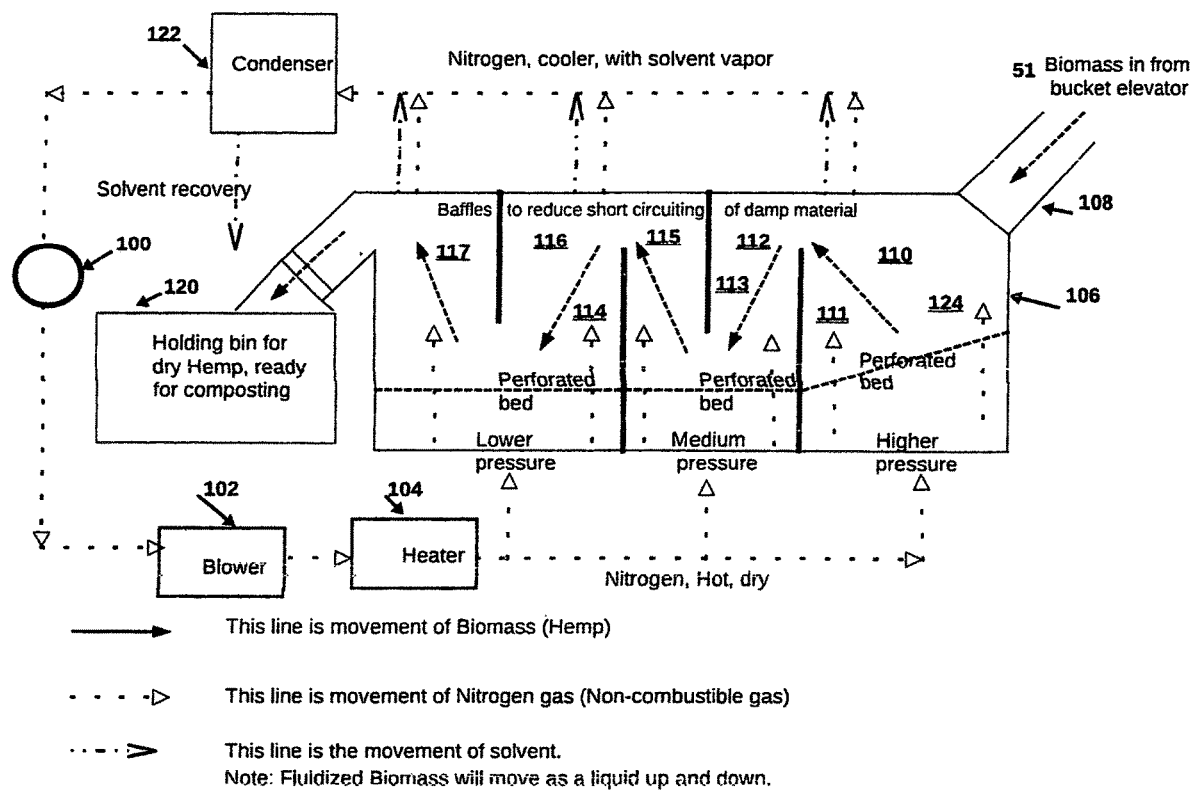
Figure 4: Concept fluidized bed dryer for hemp with closed loop Nitrogen gas

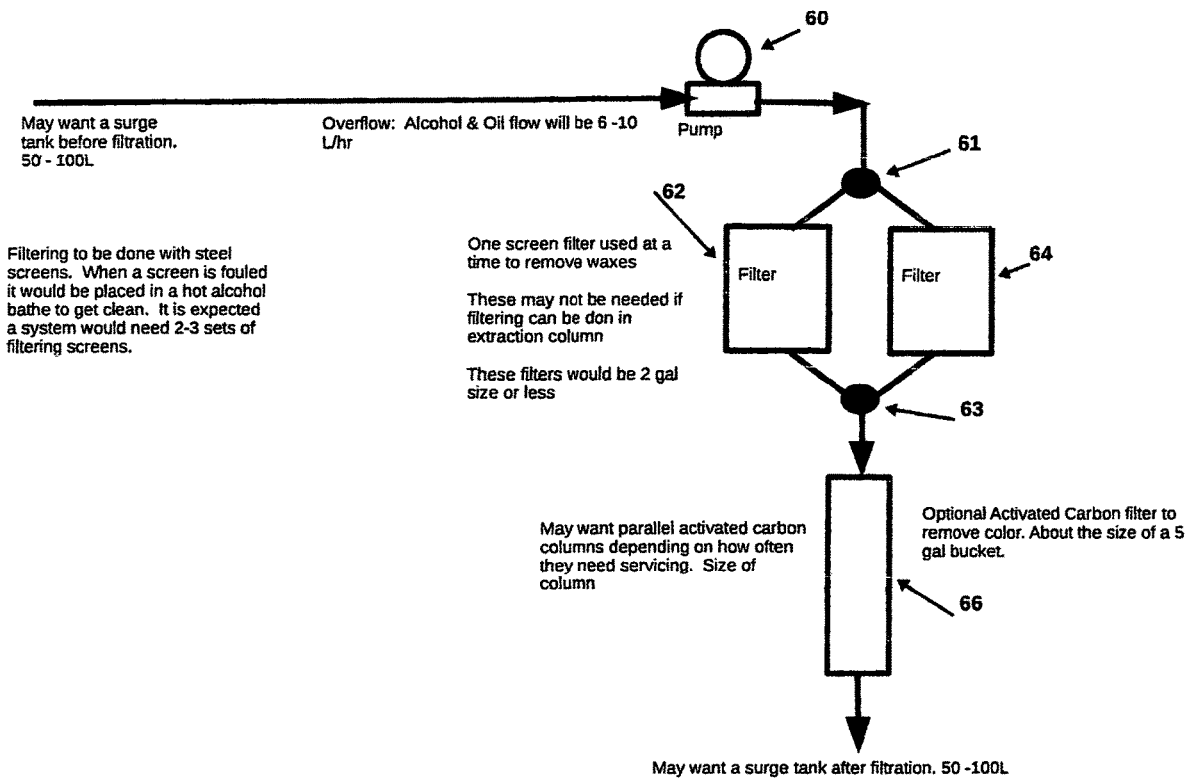
Figure 5: Filtration

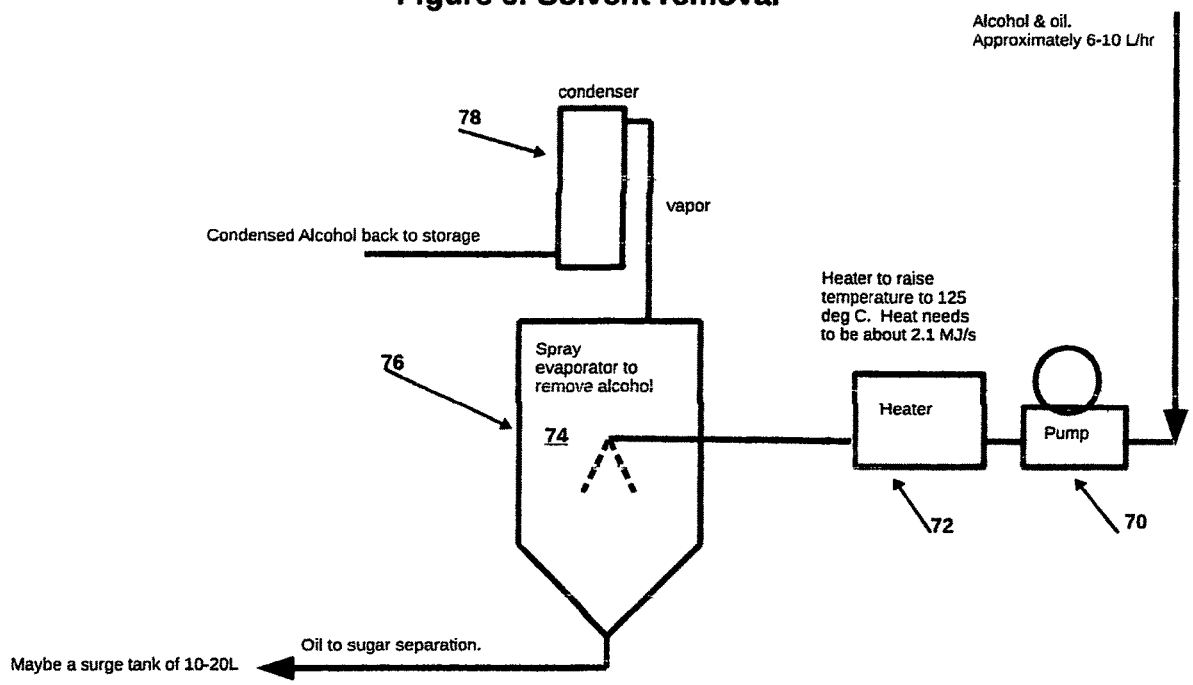

Figure 7: Sugar separation
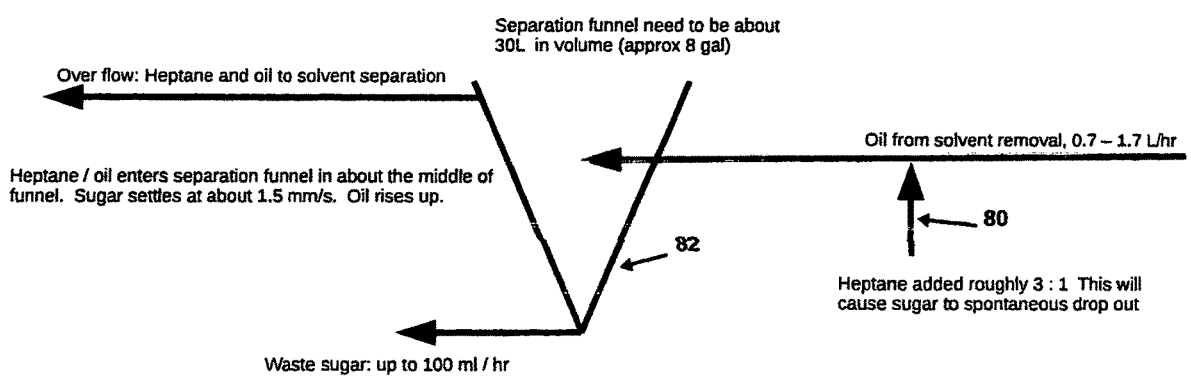

Figure 8: Solvent removal and decarboxylation
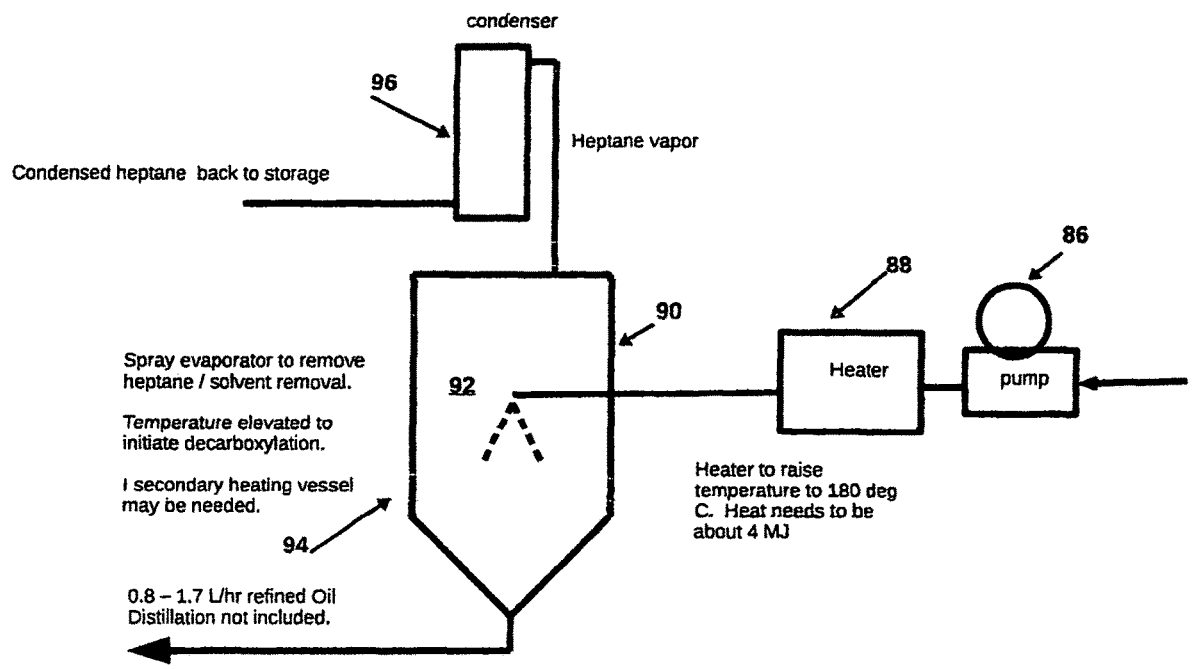

METHOD FOR SEPARATING ESSENTIAL OILS FROM BIOMASS

CROSS-REFERENCE TO RELATED APPLICATION

This application claims priority from Provisional Application Ser. No. 62/922,609, filed Aug. 19, 2019.

FIELD OF THE INVENTION

This invention relates to novel and efficient separation of essential oils, such as cannabidiol ("CBD") oil from biomass, such as the flowers of hemp plants.

BACKGROUND OF THE INVENTION

In recent years, and especially since the passage of the 2018 United States farm bill, which legalized farming of hemp, production of CBD from hemp has been gaining greatly in popularity. CBD is a cannabinoid which is marketed for various medicinal and therapeutic purposes, and is distinguished from THC, also a cannabinoid, which has psychoactive properties. CBD is extracted from the flowers of the hemp plant as an oil, which can be refined and marketed in a variety of forms.

The typical process for removing the CBD oil from the hemp flowers, after the flowers have been preprocessed by chopping, sifting and the like to remove unwanted material, employs a solvent to dissolve the CBD oil and allow it to be separated from the plant matter. One common solvent is an alcohol such as ethanol; another is carbon dioxide, and a third is an alkane such as pentane. The present invention relates to improvements in methods of using alcohol as the solvent, though the invention can be employed with other solvents as well.

Similar materials and processes are used for extraction of other essential oils from other forms of biomass. The present invention is useful to varying degrees with some of these. The invention will be described in terms of extraction of CBD oil from hemp, for simplicity, but should not be so limited.

Insofar as known, the presently preferred process for employing alcohol as the solvent to extract CBD oil from hemp is a batch process, wherein the chopped hemp flowers are simply placed in a receptacle with the alcohol, and allowed to rest. Over time, the alcohol absorbs some fraction of the CBD. The CBD-containing alcohol is decanted, and fresh alcohol is added, similarly removing a further fraction of the CBD. This process can be repeated as often as desired, with less and less CBD being removed in each step. Eventually the CBD oil, and other removed substances, such as waxes, lipids, and sugars, are separated from the alcohol, which can then be reused.

It will be appreciated that a batch process such as the above is time-consuming and relatively inefficient. With the growth of the market for CBD-containing products, there exists a demand for a more efficient, more economical process for removing CBD oil from hemp. The present invention is directed to such a process.

SUMMARY OF THE INVENTION

As opposed to the batch process described above, the present invention provides a continuous CBD extraction process. In brief, the dry hemp flowers are admitted to the upper end of an extractor assembly comprising a vertical first inner draft tube. This first inner draft tube is centered within a second outer tube of larger diameter, which communicates through a conical medial section with a third lower tube of diameter similar to the first tube. The hemp passes downwardly through this assembly, and exits through a valve at the lower extremity of the third tube, the valve opening being controlled to yield a typical residence time for the hemp of on the order of twenty minutes. The valve communicates with the lower end of an elongated inclined bucket conveyor or auger, which removes the hemp for composting or other use.

At the same time, alcohol is injected into the bottom of the third tube under moderately high pressure through a plurality, e.g. 4 to 8, of injectors. While some fraction of the alcohol will exit the valve with the hemp, and can be recovered therefrom for further use, a significant fraction of the alcohol migrates upwardly, mixing intimately with the hemp flowers and extracting the CBD oil therefrom. The alcohol and CBD oil reach the top of the outer second tube and are collected at an overflow weir, for further processing.

BRIEF DESCRIPTION OF THE DRAWINGS

The invention will be better understood if reference is made to the accompanying drawings, in which:

FIG. 1 is a schematic diagram of the entire process;

FIG. 2 is a more detailed schematic diagram of preprocessing and supply equipment;

FIG. 3 is a more detailed schematic diagram of the extractor assembly and hemp removal equipment, as briefly described above;

FIG. 4 is a schematic diagram of fluidized-bed equipment for separation of the alcohol that exits along with the hemp from the extractor assembly;

FIG. 5 is a more detailed schematic diagram of filtration equipment employed to separates waxes and lipids from the CBD oil/alcohol effluent;

FIG. 6 is a more detailed schematic diagram of equipment used to separate the alcohol from the CBD oil;

FIG. 7 is a more detailed schematic diagram of equipment used to separate sugars from the CBD oil using a heptane solvent; and FIG. 8 is a more detailed schematic diagram of equipment used to separate the heptane from the CBD oil.

DETAILED DESCRIPTION OF THE PREFERRED EMBODIMENTS

As mentioned above, FIG. 1 shows a schematic diagram of the process according to the invention for recovering CBD oil from hemp. The system described in detail in this example is capable of processing on the order of 10 kg/hr of hemp, yielding 0.8-1.7 L/hr of refined CBD oil. The system shown could readily be scaled up, with some possible modifications as discussed below.

The process begins at 10 with supply of hemp to a pug mill 12 which is used to mill the hemp to the desired size, e.g., 0.1-1.0 cm. The hemp is supplied to a conveyor belt (or auger) 14 which deposits the hemp into the upper central opening of an extractor assembly 16. The extractor assembly 16, which is further detailed below in connection with FIG. 3, comprises a cylindrical vertical first inner draft tube 40, open at both ends. This first inner draft tube 40 is centered within a second outer tube 42 of larger diameter, also cylindrical, which communicates through a conical medial section 44 with a third cylindrical lower tube 46 of diameter similar to the first tube 40. The hemp passes downwardly through this assembly. As the hemp exits the inner draft tube 40, it forms a mat 43 extending outwardly. The hemp exits through a valve 48 at the lower extremity of the third tube 46, the valve opening being controlled to yield a typical residence time for the hemp of on the order of twenty minutes.

At the same time, alcohol is injected into the bottom of the third tube under moderately high pressure, e.g. 15-30 psi, through a plurality, e.g., 4 to 8, of injectors 50. While some fraction of the alcohol will exit the valve 48 with the hemp, and can be recovered therefrom for further use, a significant fraction of the alcohol migrates upwardly, mixing intimately with the hemp flowers and extracting the CBD oil therefrom. The "liquor" comprising alcohol and CBD oil reaches the top of the outer second tube 42 and is collected at an overflow weir 52 (see FIG. 3), for further processing as detailed below.

In the example, the total volume of the extractor assembly 16 is on the order of 200 L. The oil is principally extracted in the lower portion of the extractor 16; the larger diameter upper portion helps to clarify the alcohol/oil liquor.

The hemp, with some alcohol mixed therein, exiting the extractor 16 via valve 48, is deposited on the lower extremity of an elongated inclined bucket-lift conveyor 51. An auger conveyor could be used in place of the bucket-lift conveyor. In a small-scale embodiment, the hemp reaching the upper extremity of conveyor 51 is deposited in a container having a screened lower surface, enabling some fraction of the alcohol to drain off and be reused. In the event the system is scaled-up in size for greater throughput, this assembly can be replaced with a more efficient fluidized-bed separator 106 using upwardly-directed jets of heated nitrogen (to prevent oxidization of the alcohol) to separate the hemp from the alcohol, as described below in connection with FIG. 4.

An outflow of about 6-10 L/hr of the alcohol/CBD oil liquor is expected. This is pumped by pump 60 through one of paired filters 62, 64, used alternatingly to allow cleaning, to remove waxes and lipids. The flow may then pass through an activated charcoal filter 66, to remove color.

The next step is the separation of the CBD oil from the alcohol. This is accomplished by a "flash distillation" step 68, where the stream of liquor, having been pressurized by pump 70 and heated by heater 72 to at least 125° C., is atomized at 74 into a closed volume 76. The alcohol vapor that results is condensed at 78 and returned to storage for reuse. If the solvent is not fully vaporized, the oil can be passed through additional similar stages as required (not shown) to distill the remaining solvent.

Next is removal of sugar from the CBD oil. This is accomplished by mixing 3 parts heptane with one part CBD oil, at 80. The oil and heptane mixture is then disposed in a separation funnel 82; the sugar precipitates, and is drawn off at 84.

Finally, the heptane must be removed. This accomplished by pressurizing the mixture by pump 86, heating it to at least about 180° C. in heater 88, and admitting it to a second flash distillation unit 90, in which it is atomized at 92 in a closed volume 94, after which the gaseous heptane is condensed in a condenser 96, and returned to storage for reuse. The final product is 0.8-1.7 L/hr of refined CBD oil, collected at 98.

As mentioned, FIG. 2 shows further details of the pre-processing and supply equipment. The pug mill 12 may be replaced with a different type of mill, such as a disk mill, upon experimentation. The mill is employed to reduce the hemp to particles of no more than about 1 cm.

FIG. 3 shows further details of the extraction assembly 16. In addition to the basic description of this device and its operation as described above, FIG. 3 adds several additional details. As illustrated at 56, alcohol may be drained from the lower extremity of the assembly and returned to storage. FIG. 3 also shows that the biomass removal apparatus 51 extends somewhat above the upper end of the extractor assembly 16, so that a nominal solvent level at A, established by the height of the outlet 52, is below the height of the outlet 57 of the biomass removal apparatus 51.

An important aspect of the invention is the relatively small amount of solvent used. This makes it feasible to chill the injected alcohol to between −20 and −40° C. prior to injection. Chilling the alcohol significantly reduces the amounts of wax, lipids and sugar extracted with the oil. It is also noted that a screen might be provided on the overflow outlet 52, to remove wax (wax removal from CBD oil being referred to as "winterization" by some in the art), which might allow elimination of filters 62, 64.

Some alcohol will remain absorbed in the hemp exiting the biomass removal apparatus 51, and this can usefully be recovered and reused. In a low-volume embodiment, this could be accomplished by gathering the hemp and alcohol in a drop tank with a screened lower partition, so that the alcohol drips out of the hemp biomass.

In a larger-scale plant, a fluidized-bed dryer 106 with nitrogen supplied under pressure at the lower extremity of a tank is employed to blow the alcohol out of the hemp biomass to enable collection and reuse. See FIG. 4. Nitrogen (used as a non-oxidizing medium) is supplied from a reservoir 100, pressurized by a blower 102, and heated in a heater 104. The nitrogen, at differing pressures as illustrated, is admitted to a first high-pressure chamber 110 in an enclosure 106. Biomass, e.g., hemp, is admitted to chamber 110 via a chute 108. The nitrogen passes upwardly through perforations in a bed 124. The hot, pressurized nitrogen causes the alcohol on the hemp to vaporize; it is collected in a condenser 122 and stored for reuse.

The pressurized nitrogen motivates the hemp through chamber 110, into a second chamber 112 divided from the first by a partition 111. The process continues into a third chamber 115, and a fourth 117, the chambers being defined effectively by partitions 113, 114, and 116. In each chamber the hot, pressurized nitrogen continues to purge the hemp of alcohol. As above, the alcohol is condensed and stored for reuse, which provides a substantial improvement in overall process efficiency. The dry hemp eventually reaches a bin 120, where it can be used as compost or the like.

Comparing the continuous fluidized-bed process of the invention for removing excess alcohol for reuse from hemp biomass to prior art batch processes for doing the same:

The biomass processing carried out by the prior art, so far as known, is one of the following:

A) No solvent recovery is attempted. The alcohol-soaked hemp is simply discarded. The solvent is lost by atmospheric drying, that is, evaporation.

B) The hemp may be placed in a receptacle with a perforated bottom surface, allowing the hemp to drip dry for 30-180 minutes. Some solvent is collected and can be returned to the process. The hemp is discarded, still damp. A substantial fraction of the solvent is lost to atmospheric drying.

C) The wet hemp can be placed in a heated vessel and the solvent cooked off. Depending on the vessel, this will take 1-6 hours as the hemp is not always in contact with heated surfaces. Depending on the design, it will be 50-90% efficient on recovery of solvent, as the solvent will have difficulties getting out of the mass of hemp.

The above are all batch processes, requiring substantial material handling steps. By comparison, the fluidized-bed dryer of the invention is a continuous process which should remove the solvent from the hemp in 5-30 minutes, typically about 10 minutes. This is because the damp hemp will be in turbulent contact with the rapidly-flowing hot nitrogen gas. The solvent will evaporate and carried away by the gas for efficient recovery.

The drying efficiency should be 90+%. This is because the exit port height can be set so hemp with a dry density can exit, but not wet hemp. Dry density is expect to be about 0.1 g/L whereas wet hemp should have a density of about 0.4 g/L. This means that the dry hemp will be lifted by the fluidized bed 4 times higher than wet hemp, allowing the dry hemp to be removed, while the damp hemp remains in the dryer 106 until it too becomes dry.

FIG. 5 shows details of the filtration equipment. A pump 60 pressurizes the alcohol/CBD oil liquor recovered from the extraction assembly, and passes it through one of two parallel filters 62, 64 for wax removal; plural filters are provided so that only one is in service at any given time, with the other being removed for cleaning in an alcohol bath. Y-valves 61, 63 are provided to control the flow path between the filters 62, 64. The activated carbon filter 66 may also be duplicated, for similar reasons, and be similarly valved. Surge tanks (not shown) may be provided before and/or after the filtration stage, to allow flow rate control.

FIG. 6 shows details of the "flash distillation" apparatus employed to separate out the alcohol from the alcohol/CBD oil liquor. Flash distillation is explained in detail in *Separation Process Engineering*, 4$^{th}$ ed., Phillip C. Wankat, (Prentice Hall 2017). In the present application, the liquor is pressurized by pump 70 and heated by heater 72 to 105-125° C., as described above, so that when it is atomized at nozzle 74, the alcohol vapor rises and is collected for condensation in condenser 78, and returned for reuse. The CBD oil is of higher boiling point and precipitates for supply to the next step, separation of sugar.

As far as is known to the inventors, in current CBD batch extraction processes, the alcohol is typically separated from the CBD oil in a "pot still" in which the alcohol is simply boiled off, i.e., distilled, over a lengthy period of time. A typical pot still is a 50 L glass flask heated in a water bath and operated at 0.05-0.7 bar. 1 bar is approximately 14 psi, so these stills have a vacuum of −6 to −8 psi. This is done to lower the boiling point of the solvent and allow for fast solvent removal. Such a still can remove about 50 L/hr of solvent. However, every other day the still will need to be "cooked down" and emptied of oil, which takes 3-4 hours of product time. Furthermore, the CBD oil, being exposed to heat over time (10-20 hrs) can exhibit measurable break down and degradation.

By comparison, flash distillation according to the invention is continuous. There is no down time required to empty and clean the reaction vessel 68. The exposure of the CBD oil to heat is minimal, on the order of a few minutes per stage. This allows the oil to proceed to the next stage without being degraded or broken down due to exposure to prolonged heating.

As noted above, if the solvent is not entirely removed in a single stage, similar flash distillation stages can be added in series.

FIG. 7 shows details of the next step. Heptane, which is a solvent for sugars, is added to the CBD oil in proportions of 3:1, at 80, and this mixture is admitted to a conical separation funnel 82, in which the sugar precipitates.

The heptane is then removed from the oil in another flash distillation step 94, similar to that described above. See FIG. 8. The mixture of CBD oil and heptane is pressurized by pump 86 and heated in heater 88 to at least 180° C., to vaporize the heptane when it is atomized at 92, in a closed container 90. The vaporized heptane is condensed in a condenser 96, and returned for storage and reuse.

As mentioned above, an object of the invention is to replace the conventional batch process for extracting CBD oil from hemp with a continuous process. It will be appreciated that while steps such as the introduction of hemp and injection of alcohol may be intermittent, to simplify control of the introducing equipment, the process of extraction of the CBD oil from the hemp is indeed continuous.

The extractor and biomass disposal equipment of FIG. 3 are important in implementation of this invention. These were discussed above. Further aspects and details of their operation are as follows:

The preprocessed hemp is introduced at the top of the central draft tube 40, and is directed downwardly thereby.

The upper section of the reactor vessel 42, outside the draft tube 40, is used for clarification in that biomass is removed from the CBD oil/alcohol liquor. The liquor exits the tank via an overflow weir at 52. A screen may be interposed between the tank and the weir, again to keep biomass from the downstream processing steps.

The biomass moves downwardly in the draft tube 40 and into the lower tube 46, while the alcohol moves upwardly. This counter current movement ensures good mixing and efficient extraction of the CBD oil. The rate of solvent flow is determined by the quantity of oil in the CBD oil/alcohol liquor. This might be measured using an optical sensor.

The alcohol solvent is injected at multiple locations at the bottom of the extraction vessel. The rate of flow needs to be sufficient to create an upward movement greater than the downward movement of the biomass. This creates a barrier, in effect, of alcohol and forces the oil upwardly. The injection also serves to break up any blockages of the biomass at the bottom of the extraction vessel and the inlet to the bucket conveyor.

A bucket lift 51 is less likely to become blocked up with biomass than might a screw auger device, though the latter is within the scope of the invention. The buckets have drain holes to allow alcohol to drain out of the biomass, for recovery and reuse. The bucket lift exit would be somewhat higher than the overflow weir 52, to ensure that the liquor is primarily removed via the weir.

Both the extractor vessel and the bucket lift should be liquid-tight and sealed to retain alcohol vapors. They may be positively pressurized with nitrogen to avoid fire hazard.

To compare the continuous proves of CBD oil extraction according to the present invention to the prior art batch extraction processes, as described above, the concentration of CBD oil realized in a typical batch extraction process is around 2-3% oil in the extracting solvent. This requires a solvent removal step before downstream processing.

In the continuous system of the invention, oil concentration is expected to be 20-60% of solvent in the overflow of the extraction column 16. At this concentration, de-waxing or "winterization" by simple filtration is possible without solvent removal. A clear advantage is thus presented by the invention in terms of process efficiency.

While a preferred embodiment of the invention has been described in detail, the invention should not be limited thereby, but only by the following claims.

What is claimed is:

1. A continuous process for extracting essential oils from biomass, comprising the steps of:
   providing an elongated, vertically-oriented extraction vessel, comprising an inner draft tube for receiving biomass at an upper end thereof, an outer tube of larger diameter than said inner draft tube and located concentrically around said inner draft tube and defining an outlet weir at its upper extremity, a conical midsection affixed to a lower end of said outer tube, and a lower tube affixed to a lower end of said conical midsection and having an outlet at a lower end thereof,
   providing a conveyor in sealed communication with said outlet of said lower tube, said conveyor being inclined upwardly from said outlet of said lower tube, being maintained at an angle to the vertical and having an upper outlet above said outlet weir,
   introducing biomass to the upper end of said inner draft tube, such that the biomass migrates downwardly,
   introducing a solvent for the essential oils at a lower extremity of said reactor vessel,
   allowing the solvent to migrate upwardly through the biomass, absorbing the essential oils therefrom, forming a liquor;
   collecting the liquor at said overflow weir,
   allowing the biomass to exit the lower tube at the outlet thereof and be deposited in said conveyor, and
   driving said conveyor to propel biomass from said outlet of said lower tube to the upper outlet of said conveyor.

2. The method of claim 1, comprising the further step of collecting solvent from the biomass exiting the conveyor.

3. The method of claim 1, wherein the biomass is hemp, the essential oil is CBD oil, and the solvent is alcohol.

4. The method of claim 3, comprising the further step of separating the alcohol from the CBD oil.

5. The method of claim 4, wherein said step of separating the alcohol from the CBD oil is performed by heating and pressurizing the alcohol/CBD liquor, atomizing the liquor in a closed container such that the alcohol forms a vapor, and collecting and condensing the vapor.

6. The method of claim 3, comprising the further step of filtering waxes and lipids from the liquor.

7. The method of claim 5, comprising the further step of removing sugars from the CBD oil.

8. The method of claim 7, wherein said step of removing sugars from the CBD oil is performed by mixing the CBD oil with heptane, and allowing the sugars to precipitate out of the CBD oil.

9. The method of claim 8, comprising the further step of removing the heptane from the CBD oil.

10. The method of claim 9, wherein the heptane is removed by heating and pressurizing the mixture of heptane and CBD oil, atomizing the mixture in a closed container such that the heptane forms a vapor, and collecting and condensing the vapor.

11. The method of claim 2, wherein said step of collecting solvent from the biomass exiting the conveyor is performed employing a fluidized bed dryer, wherein pressurized gas is blown through a closed chamber having a perforated bottom surface, whereby the gas separates the solvent from the biomass, whereby the solvent can be condensed for reuse.

* * * * *